United States Patent [19]

Anik

[11] Patent Number: 5,116,817
[45] Date of Patent: May 26, 1992

[54] LHRH PREPARATIONS FOR INTRANASAL ADMINISTRATION

[75] Inventor: Shabbir T. Anik, Palo Alto, Calif.

[73] Assignee: Syntex (U.S.A.) Inc., Palo Alto, Calif.

[21] Appl. No.: 587,494

[22] Filed: Sep. 20, 1990

Related U.S. Application Data

[63] Continuation of Ser. No. 20,419, Jan. 20, 1987, abandoned, which is a continuation of Ser. No. 741,312, Jun. 4, 1985, abandoned, which is a continuation-in-part of Ser. No. 448,548, Dec. 10, 1982, abandoned.

[51] Int. Cl.$^5$ ............................................. A61K 37/02
[52] U.S. Cl. ..................... 514/15; 514/800; 530/320
[58] Field of Search ................... 514/15, 800; 530/320

[56] References Cited

U.S. PATENT DOCUMENTS

| | | | |
|---|---|---|---|
| 4,118,483 | 10/1978 | König et al. | 514/15 |
| 4,156,719 | 5/1979 | Sezaki et al. | 424/118 |
| 4,261,887 | 4/1981 | Amoss et al. | 514/15 |
| 4,476,116 | 10/1984 | Anik | 514/15 |

FOREIGN PATENT DOCUMENTS 1454105 10/1976 United Kingdom.

OTHER PUBLICATIONS

Hirai et al., *International Journal of Pharmaceutics*, 9, 165–172 (1981).
Pontiroli et al., *British Medical Journal*, 284, 303–306 (1982).
Beattie et al., *Journal of Medicinal Chemistry*, 18, No. 12, 1247–1250 (1975).
Okada et al., *Journal of Pharmaceutical Science*, vol. 71, No. 12, 1367–1371 (1982).
*The Merck Index*, 9th Ed., Merck & Co., Inc., Rahway, N.J. 1976, p. 583, entry No. 4330.

*Primary Examiner*—Ronald W. Griffin
*Attorney, Agent, or Firm*—Tom M. Moran; Derek P. Freyberg; William Schmonsees

[57] ABSTRACT

The present invention relates to a novel nasal composition comprising a nona- or decapeptide having LHRH agonist or antagonist activity and a surfactant which is a bile acid or a pharmaceutically acceptable salt thereof in a buffered aqueous solution.

11 Claims, No Drawings

LHRH PREPARATIONS FOR INTRANASAL ADMINISTRATION

This application is a continuation of application Ser. No. 07/020,419, filed Jan. 20, 1987, abandoned, which is a continuation of application Ser. No. 06/741,312, filed Jun. 4, 1985, abandoned, which is a continuation-in-part of application Ser. No. 06/448,548, filed Dec. 10, 1982, abandoned.

The present invention relates to a novel LHRH formulation. More particularly, the present invention relates to an aqueous LHRH active nona-or decapeptide preparation containing a surfactant derived from a bile acid or a salt thereof which is suitable for intranasal administration.

Luteinizing hormone (LH) and follicular stimulating hormone (FSH) are released from the anterior pituitary gland under the control of the releasing hormone LHRH produced in the hypothalmic region. LH and FSH act on the gonads to stimulate the synthesis of steroid hormones and to stimulate gamete maturation. The pulsatile release of LHRH, and thereby the release of LH and FSH, control the reproductive cycle in domestic animals and humans. LHRH also affects the placenta, and the gonads indirectly in causing the release of chorionic gonadotropin (hCG).

LHRH peptides have heretofore been administered almost exclusively by injection. Other methods of administration, e.g., oral, nasal, intratracheal and rectal administration, have been investigated but because these compounds are polypeptides, these routes of administration have had little or no pharmacological effect because of poor absorption or the effect has been somewhat uncontrollable at best because of irregular absorption. When non-injection routes are used, the drug dose must be substantially increased because the amount of drug reaching the intended site of activity is greatly reduced by mechanisms ongoing in the absorption process which prevent absorption or degrade the peptides during absorption.

The nasal administration of insulin to rats is described by S. Hirai, et al, in the *International Journal of Pharmaceutics*, 9, 165-172 (1981). In this reference, aqueous insulin solutions containing a surfactant have indicated that, in certain instances, the presence of certain surfactants results in decreased serum glucose levels over control solutions comprising water and insulin. The Hirai reference discloses surfactants from a broad range of types including ethers, esters, anionic surfactants, amphoterics, bile acid salts, a glycoside and a peptidelipid. Except for a few isolated cases, the polyoxyethelene fatty acid ethers, anionic, amphoteric, bile acid salt, glycoside, and peptidelipid surfactants all showed an approximately equivalent decrement in plasma glucose levels. While the decrement in plasma glucose levels is an indirect measure of insulin absorption, it is clear that most of the surfactants tested had an equal effect on the uptake of insulin administered by the nasal route in rats.

Hirai also teaches that a solution that is about 1.0 percent by weight in glycocholate will work acceptably well when insulin is the drug to be administered. Applicant has found that such a solution will not give acceptable results for LHRH analogs. The solubility of LHRH analogs is too low in such solutions to give reasonable clinical compositions. This has been found to be a result of the difference in iso-electric points between the two drugs. Insulin has a relatively low iso-electric point of about 6.5, whereas LHRH analogs have iso-electric points greater than about 9.0, preferably between about 9.0 and 12.0.

A British Patent 1,527,605 published Oct. 4, 1978 describes the use of surfactants for enhancing insulin uptake across the nasal membrane. Hirai is one of the inventors on this patent. The effect of sodium glycocholate on the uptake of insulin administered by nasal spray to humans is reported by A. E. Ponteroli, et al, *British Medical Journal*, Vol 284, pp 303-306, (1982). Since a single surfactant was used there the relative effect of sodium glycocholate versus other surfactant on insulin uptake cannot be apprised.

It has now been found that the combination of bile acids and their pharmaceutically acceptable salts with LHRH analogs greatly enhance LHRH absorption across the nasal membranes relative to other surfactants.

The present invention provides a nasal composition comprising a nona- or decapeptide or its pharmaceutically acceptable salt having LHRH agonist or antagonist activity; and a surfactant which is bile acid or a pharmaceutically acceptable salt thereof; formulated in an aqueous solution.

In one embodiment the present invention relates to a novel nasal spray composition comprising an LHRH agonist or antagonist compound plus a surfactant which is a bile acid or a pharmaceutically acceptable salt thereof formulated in an aqueous solution which may be buffered and may contain other appropriate pharmaceutical excipients, for example, co-solvents, chelating agents, preservatives and the like.

The invention also relates to a method for enhancing the nasal uptake of a LHRH analog, which method comprises adding a surfactant which is a bile acid or a pharmaceutically acceptable salt thereof to a nasal composition comprising a nona or decapeptide or a pharmaceutically acceptable salt thereof having LHRH agonist or antagonist activity formulated in an aqueous solution.

Agonist and antagonist analogs of LHRH have been prepared and found to be useful in the control of fertility in both male and female; are useful in the reduction in accessory organ weight in male and female; will promote weight gain in domestic animals in feedlot situations; will stimulate abortion in pregnant animals; and in general act as chemical sterilants.

The natural hormone releasing hormone, LHRH, is a decapeptide comprised of naturally occuring amino acids (which have the L-configuration except for the achiral amino acid glycine). It has an iso-electric point of about 10. Its sequence is as follows:

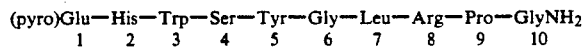

$$\text{(pyro)Glu—His—Trp—Ser—Tyr—Gly—Leu—Arg—Pro—GlyNH}_2$$
$$1 \quad 2 \quad 3 \quad 4 \quad 5 \quad 6 \quad 7 \quad 8 \quad 9 \quad 10$$

A large number of analogs of this natural material have been prepared and studied in attempts to find compounds which have greater agonist or antagonist activity.

By far the most significant modification for the enhancement of agonist activity is obtained by changing the 6-position residue from Gly to a D-amino acid. In addition, substantial increased agonist activity is obtained by eliminating the Gly—NH₂ in position 10 to afford a nonapeptide as an alkyl, cycloalkyl or fluoralkylamide or by replacing the Gly—NH₂ by an α-azaglycine amide. In yet other instances modifications have been made at positions 1 and 2 in attempts to enhance agonist activity.

In addition to the preparation of agonist analogs, a number of nona- and decapeptides have been prepared which are competitive antagonists to LHRH, all of which require deletion or replacement of the histidine residue at position 2. In general, it appears that a D-amino acid placed in the sequence at that position gives the best antagonist activity. It has also been shown that adding a modification at the 6 position, which, without the modification at position 2 results in the agonist activity noted above, enhances the antagonist activity of the 2-modified analogs. Additional increments in antagonist activity may be had by modifying positions 1, 3 and/or 10 in the already 2, 6 modified peptide. It has also been shown that N-acylation of the amino acid at position 1 is helpful.

This invention has application to LHRH and all synthetic agonist and antagonist analogs thereof. The isoelectric point of LHRH analogs are all in the range of between about 9.0 and 12.0. The patent and periodical literature is replete with nona- and decapeptides of this type. It is intended that all such compounds will be within the scope of this invention.

Nona- or decapeptides having LHRH agonist or antagonist activity are disclosed, along with processes for preparation thereof, in the following U.S. Pat. Nos. 3,813,382; 3,842,065; 3,849,389; 3,855,199; 3,886,135; 3,890,437; 3,892,723; 3,896,104; 3,901,872; 3,914,412; 3,915,947; 3,929,759; 3,937,695; 3,953,416; 3,974,135; 4,010,125; 4,018,914; 4,022,759; 4,022,760; 4,022,761; 4,024,248; 4,034,082; 4,072,668; 4,075,189; 4,075,192; 4,086,219; 4,101,538; 4,124,577; 4,124,578; 4,143,133; 4,234,571; 4,253,997; 4,292,313; 4,341,767.

LHRH analogs disclosed in these patents are incorporated herein by reference as if set out in full herein. This list is not intended to be exhaustive of all U.S. Patents convering LHRH analogs but does represent the majority; nor is this invention limited exclusively to the compounds disclosed in the recited patents.

Of the numerous LHRH analogs disclosed by the foregoing patents and in the literature in general, there are certain compounds which have been shown to be preferred for the control of fertility, enhancement or growth, treatment of prostatic cancer, for inducing abortion and other situations where LHRH agonists or antagonists have utility.

One such group of agonist compound is the group of LHRH analogs disclosed in U.S. Pat. No. 4,234,571 and represented by the following formula:

(pyro)Glu-His-V-Ser-W-X-Y-Arg-Pro-Z     (I)

and the pharmaceutically acceptable salts thereof wherein:

V is tryptophyl, phenylalanyl or 3-(1-naphthyl)-L-alanyl;

W is tyrosyl, phenylalanyl or 3-(1-pentafluorophenyl)-L-alanyl;

X is a D-amino acid residue

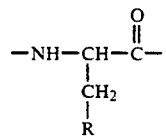

wherein R is (a) a carbocyclic aryl-containing radical selected from the group consisting of naphthyl, anthryl, fluorenyl, phenanthryl, biphenylyl, benzhydryl and phenyl substituted with three or more straight chain lower alkyl groups; or (b) a saturated carbocyclic radical selected from the group consisting of cyclohexyl substituted with three or more straight chain lower alkyl groups, perhydronaphthyl, perhydrobiphenylyl, perhydro-2,2-diphenylmethyl and adamantyl;

Y is leucyl, isoleucyl, nor-leucyl or N-methyl-lecuyl;

Z is glycinamide or —NR—R¹, wherein R¹ is lower alkyl, cycloalkyl, fluoro lower alkyl or

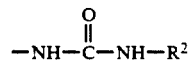

wherein R² is hydrogen or lower alkyl.

More preferred are those compounds of Formula I wherein V is tryptophyl or phenylalanyl; W is tyrosyl; X is 3-(2-naphthyl)-D-alanyl or 3-(2,4,6-trimethylphenyl)-D-alanyl; Y is leucyl or N-methyl-leucyl; and Z is glycinamide or —NHEt.

Particularly preferred compounds of Formula I are:

(pyro) Glu-His-Trp-Ser-Tyr-3-(2-naphthyl)-D-alanyl-Leu-Arg-Pro-Gly-NH₂;

(pyro) Glu-His-Trp-Ser-Tyr-3-(2-naphthyl)-D-alanyl-N-methyl-Leu-Arg-Pro-Gly-NH₂;

(pyro)Glu-His-Phe-Ser-Tyr-3-(2-naphthyl)-D-alanyl-Leu-Arg-Pro-Gly-NH₂;

(pyro) Glu-His-Trp-Ser-Tyr-3-(2,4,6-trimethylphenyl)-D-alanyl-Leu-Arg-Pro-Gly-NH₂;

(pyro) Glu-His-Trp-Ser-Tyr-3-(2-(naphthyl)-D-alanyl-Leu-Arg-Pro-NHEt;

(pyro) Glu-His-Trp-Ser-Tyr-3-(2-naphthyl)-D-alanyl-N-methyl-Leu-Arg-Pro-NHEt; and (pyro) Glu-His-Trp-Ser-Tyr-3-(2-naphthyl)-D-alanyl-Leu-Arg-Pro-Aza-Gly-NH₂; and their pharmaceutically acceptable salts.

Further particularly preferred agonist compounds from other noted U.S. Patents and reported in the periodical literature are:

(pyro) Glu-His-Trp-Ser-Tyr-D-Trp-Leu-Arg-Pro-GlyNH₂, Coy, C. D., *J. Med. Chem.*, 19, 423(1976;

(pyro) Glu-His-Trp-Ser-Tyr-D-Trp-N-Me-Leu-Arg-Pro-NHEt, Conbin, A. & Bex, F. J., "LHRH Peptides as Female and Male Contraceptives," Shelton, J. D. & Sciarra, J. J., Eds., Harper & Row, Philadelphia (1981), pp 68-84;

(pyro) Glu-His-Trp-Ser-Tyr-D-Trp-Leu-Arg-Pro-NHEt; Rivier, J. et al, "Peptides: Chemistry, Structure and Biology—Proceedings of the Fourth American Peptide Symposium," R. Walter & J. Meienhofer, Eds, (1975) Ann Arbor Science Publications, p 863-870;

(pyro) Glu-His-Trp-Ser-Tyr-D-Ala-Leu-Arg-Pro-GlyNH₂, U.S. Pat. No. 3,914,412;

(pyro) Glu-His-Trp-Ser-Tyr-D-Leu-Leu-Arg-Pro-NHEt; Fujino, M. et al, *Biochem. Biophys. Res. Commun.*, 60, 406 (1974);

(pyro) Glu-His-Trp-Ser-Tyr-D-Leu-Leu-Arg-Pro-GlyNH₂, U.S. Pat. No. 3,914,412;

(pyro) Glu-His-Trp-Ser-Tyr-D-Ser(t-But)-Leu-Arg-Pro-NHEt, U.S. Pat. No. 4,024,248, and Konig, W., et al, "Peptides: Chemistry, Structure and Biology—Proceedings of the Fourth American Peptide Symposium," R. Walter & J. Meienhofer, Eds, (1975), Ann Arbor Science Publications, p 883–888;

(pyro) Glu-His-Trp-Ser-Tyr-D-Ser (t-But)-Leu-Arg Pro-AzaGly, Dutta, A. S., et al, *Biochem. Biophys. Res. Commun.* 81, 382 (1978);

(pyro) Glu-His-Trp-Ser-Tyr-D-His(Bzl)-Leu-Arg-Pro-NHEt, Vale, W. et al, "Peptides: Studies and Biological Function—Proceedings of the Sixth American Peptide Symposium," E. Gross & J. Meienhofer, Eds, Pierce Chem Co. (1979) pp 781–793;

(pyro) Glu-His-Trp-Ser-Tyr-D-pentamethyl-Phe-Leu-Arg-Pro-GlyNH₂, Coy, D. H., "Clinical Neurological Endocrinology—A Pathological Physical Approach," G. Tol Ed, (1979) p 83; and (pyro) Glu-His-Trp-Ser-Tyr-3-(2-naphthyl)-D-alanyl-Leu-Arg-Pro-GlyNH₂, Nestor, J., Jr. et al, *J. Med. Chem.*, 25, 795 (1982).

Preferred antagonist analogs of LHRH are the nona- and decapeptides from U.S. Pat. No. 4,341,767 and U.S. applications Ser. Nos. 387,101 filed Jun. 10, 1982, now abandoned, 451,671 filed Dec. 21, 1982, now U.S. Pat. No. 4,481,190, 472,692 filed Mar. 7, 1983, now U.S. Pat. No. 4,581,169 and 495,226 filed May 20, 1983, now U.S. Pat. No. 4,667,014 and related foreign patent applications as set out in the Schedule situated before the claims in this specification.

Such antagonists include those of Formula (II):

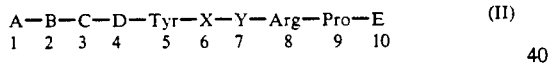

and the pharmaceutically acceptable salts thereof, wherein:

X is N,N'-guanido-disubstituted-D-argininyl or D-homoargininyl, D-argininyl, D-lysyl, or D-alanyl residue wherein one hydrogen on C-3 of the D-alanyl is replaced by:

a) a carbocyclic aryl-containing radical selected from the group consisting of phenyl substituted with three or more straight chain lower alkyl or alkoxy groups, trifluoromethyl, naphthyl, anthryl, fluorenyl, phenanthryl, biphenylyl and benzhydryl; or b) a saturated carbocyclic radical selected from the group consisting of cyclohexyl substituted with three or more straight chain lower alkyl groups, perhydronaphthyl, perhydrobiphenylyl, perhydro-2,2-diphenylmethyl, and adamantyl; or c) a heterocyclic aryl containing radical selected from the group consisting of radicals represented by the following structural formulas:

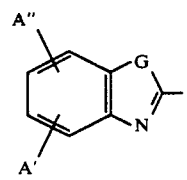

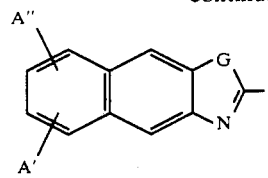

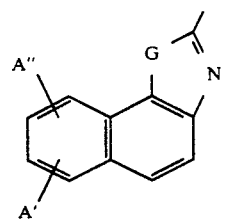

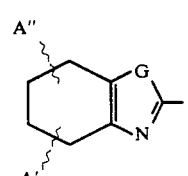

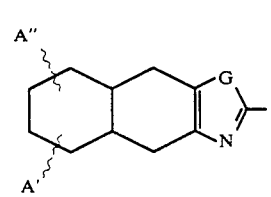

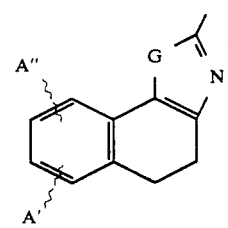

wherein A" and A' are independently selected from the group consisting of hydrogen, lower alkyl, chlorine, and bromine, and G is selected from the group consisting of oxygen, nitrogen, and sulfur;

A is an amino acyl residue selected from the group consisting of L-pyroglutamyl, D-pyroglutamyl, N-acyl-L-prolyl, N-acyl-D-prolyl, N-acyl-D-tryptophanyl, N-acyl-D-phenylalanyl, N-acyl-D-p-halophenylalanyl, N-acyl-D,L-seryl, N-acyl-D,L-threonyl, N-acyl-glycyl, N-acyl-D,L-alanyl, N-acyl-L-alkylprolyl, and N-acyl-X wherein X is as defined previously;

B is an amino acyl residue selected from the group consisting of D-phenylalanyl, D-p-halophenylalanyl, 2,2-diphenylglycyl, and X wherein X is as defined previously;

C is an amino acyl residue selected from the group consisting of L-tryptophanyl, D-tryptophanyl, D-phenylalanyl, D-phenylalanyl and X wherein X is as defined above;

D is an amino acyl residue selected from the group consisting of L-seryl, and D-alanyl;

Y is an amino acyl residue selected from the group consisting of L-leucyl, L-norleucyl and L-norvalyl;

E is D-alanyl, glycinamide or —NH—R¹, wherein R¹ is lower alkyl, cycloalkyl, fluoro lower alkyl or —NH—CO—NH—$R^2$ wherein $R^2$ is hydrogen or lower alkyl; are disclosed.

Those embodiments of Formula II most particularly preferred are those wherein the A group N-acyl is N—Ac, especially:

N-Ac-Pro-D-p-F-Phe-D-Nal(2)-Ser-Tyr-D-Nal(2)-Leu-Arg-Pro-GlyNH$_2$; and

N-Ac-Pro-D-p-Cl-Phe-D-Nal(2)-Ser-Tyr-D-Nal(2)-Leu-Arg-Pro-GlyNH$_2$.

Also particularly preferred are the following compounds which are disclosed in the noted patent and periodical literature:

N-Ac-$\Delta^3$Pro-D-p-F-Phe-D-Nal(2)-Ser-Tyr-D-Nal(2)-Leu-Arg-Pro-GlyNH$_2$, Rivier, J., et al, "LHRH Peptides as Female and Male Contraceptives," G. I. Zatuchni, J. D. Shelton & J. J. Sciarra, Eds, Harper & Row, Philadelphia (1981), pp 13-23;

N-Ac-$\Delta^3$Pro-D-p-Cl-Phe-D-Trp-Ser-Tyr-D-Trp-N-Me-Leu-Arg-Pro-GlyNH$_2$, Rivier, J., et al, *Science*, 210, 93 (1980);

N-Ac-D-p-Cl-Phe-D-p-Cl-Phe-D-Trp-Ser-Tyr-D-Trp-Leu-Arg-Pro-D-AlaNH$_2$, Erchegyi, *Peptides*, 2, 251 (1981);

N-Ac-D-p-Cl-Phe-D-p-Cl-Phe-D-Trp-Ser-Tyr-D-Arg-Leu-Arg-Pro-D-AlaNH$_2$, Coy, D. H., *Endocrinology*, 110, 1445 (1982); and N-Ac-D-Nal(2)-D-p-F-Phe-D-Trp-Ser-Tyr-D-Arg-Leu-Arg-Pro-GlyNH$_2$, Rivier, J., et al, *Contraceptive Delivery Systems*, 3, 67 (1982).

Also useful are compounds of formula II but wherein A is N-acyl-$\Delta^3$-Pro, which can be prepared in analogous manner to the corresponding compounds of Rivier referenced above.

Such antagonists also include those of formula

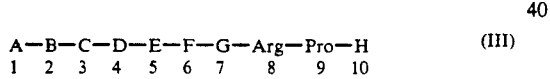

and the pharmaceutically acceptable salts thereof, wherein:

A is an amino acyl residue selected from the group consisting of L-pyroglutamyl, D-pyroglutamyl, N-acyl-D,L-tryptophanyl, N-acyl-glycyl, N-Ac-D,L-$\Delta^{3,4}$-prolyl, N-Ac-D,L-prolyl, N-Ac-L-alkylprolyl, N-Ac-D,L-phenylalanyl, N-Ac-D,L-p-chlorophenylalanyl, N-Ac-D,L-seryl, N-Ac-D,L-threonyl, N-Ac-D,L-alanyl, 3-(1-naphthyl)-D,L-alanyl, 3-(2-naphthyl)-D,L-alanyl, 3-(2,4,6-trimethylphenyl)-D,L-alanyl, 3-(4-trifluoromethylphenyl)-D,L-alanyl, 3-(9-anthryl)-D,L-alanyl, 3-(2-fluorenyl)-D,L-alanyl, and 3-(Het)-D,L-alanyl wherein Het is a heterocyclic aryl containing radical selected from

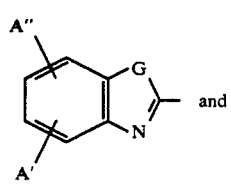

and

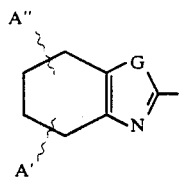

wherein A″ and A′ are independently selected from the group consisting of hydrogen, lower alkyl, chlorine and bromine, and G is selected from the group consisting of oxygen, nitrogen and sulfur;

B is an amino acyl residue selected from the group consisting of D-phenylalanyl, D-p-Cl-phenylalanyl, D-p-F-phenylalanyl, D-p-nitrophenylalanyl, 3-(3,4,5-trimethoxyphenyl)-D-alanyl, 2,2-diphenylglycine, D-α-methyl-p-Cl-phenylalanine and 3-(2,4,6-trimethylphenyl)-D-alanyl;

C is an amino acyl residue selected from the group consisting of L-tryptophanyl, D-tryptophanyl, D-phenylalanyl, D-Me$_5$phenylalanyl, 3-(2-pyridyl)-D-alanyl, 3-(3-pyridyl)-D-alanyl, 3-(4-pyridyl)-D-alanyl, 3-(1-naphthyl)-D-alanyl, and 3-(2-naphthyl)-D-alanyl;

D is an amino acyl residue selected from the group consisting of L-seryl, and D-alanyl;

E is an amino acyl residue selected from the group consisting of L-phenylalanyl and L-tyrosyl;

F is an amino acyl selected from the group consisting of the radicals derived from amino acids represented by the following structural formulas:

a)

wherein n is 1 to 5;

$R_1$ is alkyl of 1 to 12 carbon atoms, —NRR$_3$ wherein R is hydrogen or alkyl of 1 to 4 carbon atoms, R$_3$ is alkyl of 1 to 12 carbon atoms, cycloalkyl, phenyl, benzyl, —(CH$_2$)$_n$-morpholino or —(CH$_2$)$_n$N(R$_4$)$_2$ wherein n is 1 to 5 and R$_4$ is lower alkyl;

$R_2$ is hydrogen or $R_3$; or $R_1$ and $R_2$ comprise a ring represented by the following structural formulas:

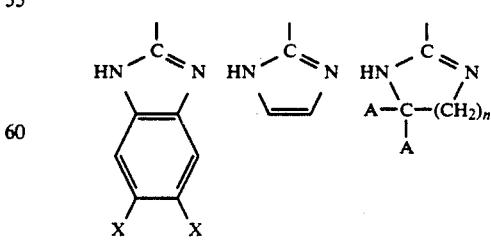

wherein n is 1 to 7; A is hydrogen, alkyl of 1 to 6 carbon atoms or cycloalkyl; and X is halo or A or b)

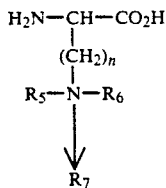

(III)

wherein $R_5$ is alkyl of 1 to 6 carbon atoms, benzyl, phenylethyl, cyclohexyl, cyclopentyl; and $R_6$ and $R_7$ are hydrogen or alkyl of 1 to 4 carbon atoms; and n is the integer 2–5; or c) a substituent of the formula

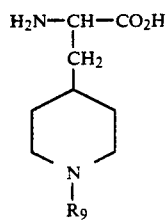

(VI)

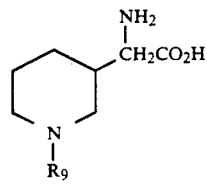

(VII)

wherein $R_9$ is hydrogen, alkyl of 1 to 12 carbon atoms, phenyl or phenylloweralkyl;

G is an amino acyl residue selected from the group consisting of L-leucyl, L-norleucyl and L-norvalyl;

H is D-alaninamide, D-leucinamide, glycinamide or $-NHR_5$ wherein $R_5$ is lower alkyl, cycloalkyl, fluoro lower alkyl, or $NHCONH-R_{10}$ wherein $R_{10}$ is hydrogen or lower alkyl; and the pharmaceutically acceptable salts thereof.

Preferred examples of such antagonists include:

N-Ac-D-Nal(2)-D-pCl-Phe-D-Trp-Ser-Tyr-D-Deh-Leu-Arg-Pro-D-AlaNH$_2$;

N-Ac-D-Nal(2)-D-pCl-Phe-D-Trp-Ser-Tyr-D-Deh-Leu-Arg-Pro-GlyNH$_2$; and

N-Ac-D-Nal(2)-D-pF-Phe-D-Trp-Ser-Tyr-D-Deh-Leu-Arg-Pro-GlyNH$_2$ and their pharmaceutically acceptable salts, and wherein D-Deh represents the residue of the amino acid N,N'-guanido-diethyl-D-homoarginine.

The amount of peptide present in the nasal formulation will often be between 0.005 and 5 milligrams per ml of solution, particularly with agonist peptides. Preferably, with agonist peptides there will be present an amount of 0.05 to 4 milligrams per ml, but most preferably the LHRH analog will be present in an amount of 0.1 to 3.0, preferrably 1.5 to 2.5, milligrams per ml. With antagonist peptides, often higher concentrations will be used, such as 5 to 100 mg/ml, more often 5 to 20, for example 5–10 mg/ml.

The agent which is responsible for enhancing the absorption of LHRH compounds across the nasal membrane are bile acid surfactants, and their pharmaceutically acceptable salts.

These acids are, for example, glycocholic acid, cholic acid, taurocholic acid, cholanic acid, ethocholic acid, desoxycholic acid, chenodesoxycholic acid and dehydrocholic acid; also glycodeoxy-cholic acid. One or more acids or salts, but preferably a single pharmaceutically acceptable acid salt, is added to the aqueous solution.

The pharmaceutically acceptable surfactant salts will be any salt which retains the phenomena of enhanced peptide absorption, as well as the compound's surfactant characteristics, and which are not deleterious to the subject or otherwise contraindicated. Such salts are for example those salts derived from inorganic bases which include sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, tromethamine, dicyclohexylamine, choline and caffeine.

More preferably, the surfactant used in the practice of this invention will be an alkali metal salt of glycocholic acid, most preferably sodium glycocholate.

The amount of surfactant used for the practice of this invention will be some amount which increases the absorption of LHRH peptides over that of other surfactants which also may enhance peptide absorption to a certain degree. It has been found that such an amount is often in the range between 0.2 and 15%, more often 0.2 to 5 percent by weight/volume of the solution. It is preferred that the surfactant be present in an amount between about 0.5 to 4 percent by weight volume, conveniently about 1 to 3 percent by weight volume, preferably about 2 percent by weight volume.

The subject nasal formulations will be formulated in water but more preferably it will be formulated in a solution buffered to a pH of between about 3.0 and 8.0, most preferably pH 5.0–5.4, by means of some pharmaceutically acceptable buffer system. Any pharmaceutically acceptable buffering system capable of maintaining a pH in the denoted range may be used for the practice of this invention. A typical buffer will be, for example, an acetate buffer, a phosphate buffer, a citrate buffer, a succinate buffer or the like. The buffer of choice herein is an acetate buffer in a concentration of between 0.005 and 0.1 molar, most preferably 0.02 molar. Water or buffer solution is added in a quantity sufficient to make volume.

Other materials such as preservatives, salts to achieve the tonic value of tissue, or other additives indicated by known nasal formulation chemistry may be added to these formulations. Particularly advantageous other such materials include surfactants, suitably non-ionic surfactants such as the polysorbates, in concentrations suitably in the range 0.1 to 5, more suitably 0.25 to 2% weight volume.

It has been found that often to obtain enhanced solubility and stability, the molar ratio of bile acid to peptide is usefully ≧20:1, such as ≧25:1.

In one suitable embodiment, the present invention relates to a nasal spray composition having enhanced LHRH polypeptide absorption comprising 0.005 to 5 mg/ml of a nona- or decapeptide or its pharmaceutically acceptable salt having LHRH agonist or antagonist activity; 0.2 to 5% by weight/volume of a surfactant which is a bile acid or a pharmaceutically acceptable salt thereof; and a buffered aqueous solution in a quantity sufficient to make volume.

In a further suitable embodiment, this invention also relates to a method for the nasal uptake of LHRH which method comprises adding from 1.5 to 5 percent, preferably 1.5 to 2.5, most preferably about 2.0, weight/volume of glycocholate or a pharmaceutically acceptable salt thereof to a nasal spray composition comprising 0.005 to 5 mg/ml of a nona- or decapeptide or its pharmaceutically acceptable salt having LHRH agonist or antagonist activity; and buffered aqueous solution in a quantity sufficient to make volume.

The invention also provides a process for preparing the nasal compositions of the invention, which comprises bringing into aqueous solution the peptide and the surfactant. As will be clear from the foregoing, this process may be carried out in known manner for preparing nasal aqueous compositions. Suitably, the peptide is first dissolved in buffer, and then added to the surfactant, the pH adjusted as required, and the volume made up to the desired level. Additional components can be added in at any convenient stage in the process.

The nasal compositions of this invention may be administered in conventional manner. For example, sufficient composition to deliver an effective dose of LHRH analog is administered to the nostrils, conveniently in a divided dose being administered to each nostril, suitably by means of a spray. Suitably a spray bottle with a metered dose (conveniently 100 μl per spray) spray attachment is used.

The invention is illustrated by the following nonlimiting examples.

EXAMPLE 1

6.25 milligrams of (pyro)Glu-His-Trp-Ser-Tyr-3-(2-naphthyl)-D-alanyl-Leu-Arg-Pro-Gly-NH$_2$ were dissolved in 5 ml of a 0.02 molar acetate buffer solution having a pH of about 5.2 in a volumetric flask. Two hundred milligrams of sodium glycocholate were then dissolved in this solution which is brought almost to volume, the pH adjusted to 5.2 plus or minus 0.2 and then a volume of buffer added in a quantity sufficient to make 10 ml.

EXAMPLE 2

1 mg of (pyro) Glu-His-Trp-Ser-Tyr-3- (2-naphthyl)-D-alanyl-Leu-Arg-Pro-Gly-NH$_2$ was dissolved in 50 ml of a 0.02 molar acetate buffer solution having a pH of about 5.2, and was added to a solution containing 500 mg of sodium glycocholate, the pH adjusted to 5.2±0.2, and then a volume of buffer added in a quantity sufficient to make 100 ml.

EXAMPLE 3

2 mg of (pyro) Glu-His-Trp-Ser-Tyr-3- (2-naphthyl)-D-analyl-Leu-Arg-Pro-Gly-NH$_2$ was dissolved in 5 ml of a 0.02 molar phosphate buffer having a pH of about 7.0, and was added to a solution containing 75 mg of sodium glycodeoxy-cholate, the pH adjusted to 7.0±0.2, and then a volume of buffer added in a quantity sufficient to make 10 ml.

EXAMPLE 4

50 mg of N-Ac-D-Nal(2)-D-pCl-Phe-D-Trp-Ser-Tyr-D-Deh-Leu-Arg-Pro-D-AlaNH$_2$ was dissolved in 5 ml of a 0.02 molar acetate buffer solution having a pH of about 5.2, and was added to a solution containing 500 mg of sodium glycocholate the pH adjusted to 5.2±0.2, and then a volume of buffer added in a quantity sufficient to make 10 ml.

EXAMPLE 5

The procedure of Example 2 was repeated, but using 17.50 mg of peptide and 2000 mg of sodium glycocholate.

EXAMPLE 6

The procedure of Example 2 was repeated, but using 12.5 mg of peptide and 200 mg of sodium glycocholate.

EXAMPLE 7

The procedure of Example 2 was repeated, but 0.5% (w/v) of Polysorbate 20 (polyoxyethylene 20 sorbitan monolaurate) was also incorporated in the solution.

EXAMPLE 8

The procedure of Example 2 was repeated, but using 10 mg of peptide and 150 mg of sodium glycocholate.

EXAMPLE 9

This example shows the effect of sodium glycocholate concentration on LHRH solubility in standard vehicle.

| AMOUNT OF GLYCOCHOLATE (percent) | SOLUBILITY OF LHRH ANALOG mg/ml |
|---|---|
| 0.25 | 0.4 |
| 0.50 | 0.1 |
| 0.75 | 0.4 |
| 1.0 | 0.7 |
| 1.25 | 1.0 |
| 1.50 | 1.3 |
| 1.75 | 1.7 |
| 2.0 | 2.0 |

This example shows the effect of increasing the amount of glycocholate on the solubility of LHRH analogs. In particular, the solubility of LHRH shows a minimum between 0.25 and 0.75 percent glycocholate. It is not until the concentration of glycocholate is as high as 1.25 percent that the concentration of LHRH analog can exceed 1.0 mg/ml.

Note, in the Examples the peptides were used in the form of their acetate salts.

BIOLOGICAL DATA

The enhancement of absorption of (pyro)Glu-His-Trp-Ser-Tyr-3-(2-naphthyl)-D-alanyl-Leu-Arg-Pro-Gly-NH$_2$ by sodium glycocholate is illustrated in the following Table I.

TABLE 1

| FORMULATION | DRUG CONC MG/ML | AVG DOSE PER MONKEY μG | PEAK PLASMA LEVEL NG/ML |
|---|---|---|---|
| STANDARD NASAL | 0.625 | 133 | 0.23 (0.08) |
| +1% SODIUM GLYCOCHOLATE | 0.625 | 120 | 11.1 (2.13) |
| SUBCUTANEOUS | | 5 | 1.9 (0.35) |

[Numbers in parenthesis are standard error. Standard nasal formulation is the peptide dissolved in acetate buffer, and at the same pH as the test formulation, but not including the sodium glycocholate.]

Further absorption tests were carried out in monkeys, as reported below in Table 2:

TABLE 2

| FORMULATION | DRUG CONC MG/ML | AVG DOSE PER MONKEY μG | PEAK PLASMA LEVEL NG/ML |
|---|---|---|---|
| STANDARD NASAL | 1.25 | 272 | 1.84 |
| +2% SODIUM GLYCOCHOLATE | 1.25 | 243 | 26.4 |
| +1% SODIUM GLYCOCHOLATE AND 0.5% POLYSORBATE 20 | 0.625 | 123 | 5.5 |

NASAL TOXICITY

The composition of Example 5 was administered to Beagle dogs intranasally at a dose of 0.4 ml per dog per day for 28 days. The nasal cavities of the dogs were examined, and no changes attributable to the composition were observed.

What is claimed is:

1. An aqueous composition for the nasal administration of LHRH analogs comprising:
   an effective amount of an LHRH agonist or antagonist, or a pharmaceutically acceptable salt thereof; and from about 0.2 to about 15 weight percent of a bile acid surfactant, or a pharmaceutically acceptable salt thereof in aqueous solution.

2. A composition according to claim 1 which is a nasal spray composition comprising:
   0.005 to 5 mg/ml of an LHRH agonist or its pharmaceutically acceptable salt or 5 to 100 mg/ml of an LHRH antagonist or its pharmaceutically acceptable salt; and
   1.5 to 5 percent by weight/volume of a bile acid surfactant or a pharmaceutically acceptable salt thereof; in a buffered aqueous solution.

3. A composition according to claim 2 wherein the LHRH compound is an agonist represented by the formula (pyro)Glu-His-V-Ser-W-X-Y-Arg-Pro-Z     (I)

and the pharmaceutically acceptable salts thereof wherein:
   V is tryptophyl, phenylalanyl or 3-(1-naphthyl)-L-ala-nyl;
   W is tyrosyl, phenylalanyl or 3-(pentafluorophenyl)-L-alanyl;
   X is a D-amino acid residue

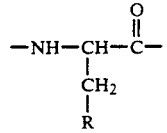

wherein R is
   (a) a carbocyclic aryl-containing radical selected from the group consisting of naphthyl, anthryl, fluorenyl, phenanthryl, biphenylyl, benzhydryl and phenyl substituted with three or more straight chain lower alkyl groups; or
   (b) a saturated carbocyclic radical selected from the group consisting of cyclohexyl substituted with three or more straight chain lower alkyl groups, perhydronaphthyl, perhydrobiphenylyl, perhydro-2,2-diphenylmethyl and adamantyl;
   Y is leucyl, isoleucyl, nor-leucyl or N-methyl-leucyl;
   Z is glycinamide or —NR—R$^1$, wherein R$^1$ is lower alkyl, cycloalkyl, fluoro lower alkyl or

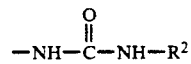

wherein R$^2$ is hydrogen or lower alkyl and the surfactant is an alkali metal salt of a bile acid.

4. A composition according to claim 3 wherein said LHRH agonist is (pyro)Glu-His-Trp-Ser-Tyr-3-(2-naphthyl)-D-alanyl-Leu-Arg-Pro-Gly-NH$_2$ or a pharmaceutically acceptable salt thereof.

5. A composition according to claim 4 wherein said pharmaceutically acceptable salt is an acetate.

6. A composition according to claim 4, wherein the LHRH agonist is present in an amount of 0.05 to 4 milligrams/ml and said surfactant is sodium glycocholate which is present in an amount of 2.0 to 4 percent weight/volume.

7. A composition according to claim 1 wherein the LHRH analog is an antagonist having the formula A—B—C—D—Tyr—X—Y—Arg—Pro—E     (II)
   1  2  3  4      5   6  7     8    9  10 and the pharmaceutically acceptable salts thereof, wherein:
   X is N,N'-guanido-disubstituted-D-argininyl or D-homargininyl, D-argininyl, D-lysyl, or D-alanyl residue wherein one hydrogen on C-3 of the D-alanyl is replaced by:
   a) a carbocyclic aryl-containing radical selected from the group consisting of phenyl substituted with three or more straight chain lower alkyl or alkoxy groups, trifluoromethyl, naphthyl, anthryl, fluorenyl, phenanthryl, biphenylyl and benzhydryl; or
   b) a saturated carbocyclic radical selected from the group consisting of cyclohexyl substituted with three or more straight chain lower alkyl groups, perhydronaphthyl, perhydrobiphenylyl, perhydro-2,2-diphenylmethyl, and adamantyl; or
   c) a heterocyclic aryl containing radical selected from the group consisting of radicals represented by the following structural formulas:

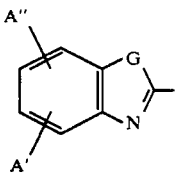

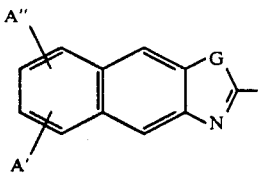

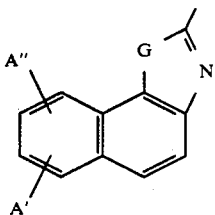

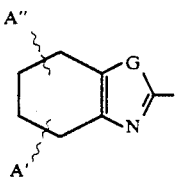

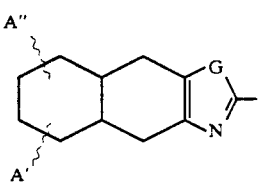

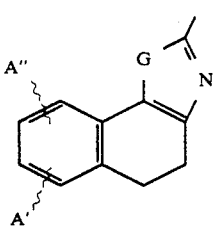

wherein A" and A' are independently selected from the group consisting of hydrogen, lower alkyl, chlorine, and bromine, and G is an atom selected from the group consisting of oxygen, nitrogen, and sulfur;

A is an amino acyl residue selected from the group consisting of L-pyroglutamyl, D-pyroglutamyl, N-acyl-L-prolyl, N-acyl-D-prolyl, N-acyl-D-tryptophanyl, N-acyl-D-phenylalanyl, N-acyl-D-p-halophenylalanyl, N-acyl-D,L-seryl, N-acyl-D,L-threonyl, N-acyl-glycyl, N-acyl-D,L-alanyl, N-acyl-L-alkylprolyl, and N-acyl-X wherein X is as defined previously;

B is an amino acyl residue selected from the group consisting of D-phenylalanyl, D-p-halophenylalanyl, 2,2-diphenylglycyl, and X wherein X is as defined previously;

C is an amino acyl residue selected from the group consisting of L-tryptophanyl, D-tryptophanyl, D-phenylalanyl, D-phenylalanyl and X wherein X is as defined above;

D is an amino acyl residue selected from the group consisting of L-seryl, and D-alanyl;

Y is an amino acyl residue selected from the group consisting of L-leucyl, L-norleucyl and L-norvalyl;

E is D-alanyl, glycinamide or —NH—R$^1$, wherein R$^1$ is lower alkyl, cycloalkyl, fluoro lower alkyl or —NH—CO—NH—R$^2$ wherein R$^2$ is hydrogen or lower alkyl.

8. A composition according to claim 1, wherein the LHRH analog is an antagonist having the formula

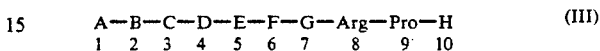

and the pharmaceutically acceptable salts thereof, wherein:

A is an amino acyl residue selected from the group consisting of L-pyroglutamyl, D-pyroglutamyl, N-acyl-D,L-tryptophanyl, N-acyl-glycyl, N-Ac-D,L-$\Delta^{3,4}$-prolyl, N-Ac-D,L-prolyl, N-Ac-L-alkylprolyl, N-Ac-D,L-phenylalanyl, N-Ac-D,L-p-chlorophenylalanyl, N-Ac-D,L-seryl, N-Ac-D,L-threonyl, N-Ac-D,L-alanyl, 3-(1-naphthyl)-D,L-alanyl, 3-(2-naphthyl)-D,L-alanyl, 3-(2,4,6-trimethylphenyl)-D,L-alanyl, 3-(4-trifluoromethylphenyl)-D,L-alanyl, 3-(9-anthryl)-D,L-alanyl, 3-(2-fluorenyl)-D,L-alanyl, and 3-(Het)-D,L-alanyl wherein Het is a heterocyclic aryl containing radical selected from

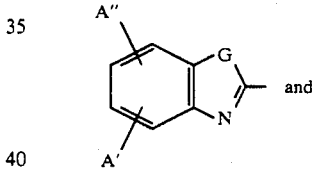 and

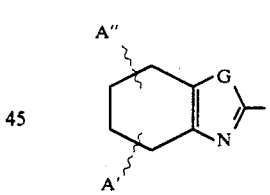

wherein A" A' are independently selected from the group consisting of hydrogen, lower alkyl, chlorine and bromine, and G is an atom selected from the group consisting of oxygen, nitrogen and sulfur;

B is an amino acyl residue selected from the group consisting of D-phenylalanyl, D-p-Cl-phenylalanyl, D-p-F-phenylalanyl, D-p-nitrophenylalanyl, 3-(3,4,5-trimethoxyphenyl)-D-alanyl, 2,2-diphenylglycine, D-α-methyl-p-Cl-phenylalanine and 3-(2,4,6-trimethylphenyl)-D-alanyl;

C is an amino acyl residue selected from the group consisting of L-tryptophanyl, D-tryptophanyl, D-phenylalanyl, D-Me$_5$phenylalanyl, 3-(2-pyridyl)-D-alanyl, 3-(3-pyridyl)-D-alanyl, 3-(4-pyridyl)-D-alanyl, 3-(1-naphthyl)-D-alanyl, and 3-(2-naphthyl)-D-alanyl;

D is an amino acyl residue selected from the group consisting of L-seryl, and D-alanyl;

E is an amino acyl residue selected from the group consisting of L-phenylalanyl and L-tyrosyl;

F is an amino acyl selected from the group consisting of the radicals represented by the following structural formulas:

a)

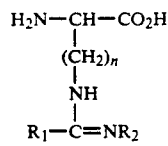

wherein n is 1 to 5;

$R_1$ is alkyl of 1 to 12 carbon atoms, $-NRR_3$ wherein R is hydrogen or alkyl of 1 to 4 carbon atoms, $R_3$ is alkyl of 1 to 12 carbon atoms, cycloalkyl, phenyl, benzyl, $-(CH_2)_n$—morpholino or $-(CH_2)_nN(R_4)_2$ wherein n is 1 to 5 and $R_4$ is lower alkyl;

$R_2$ is hydrogen or $R_3$; or $R_1$ and $R_2$ comprise a ring represented by the following structural formulas:

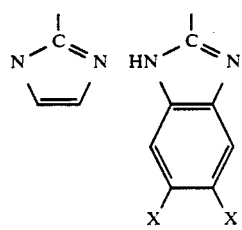

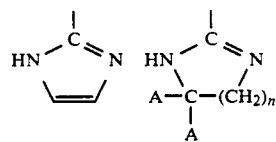

wherein n is 1 to 7; A is hydrogen, alkyl of 1 to 6 carbon atoms or cycloalkyl; and X is halo or A or b)

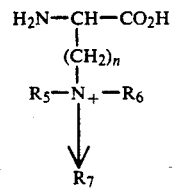

wherein $R_5$ is alkyl of 1 to 6 carbon atoms, benzyl, phenylethyl, cyclohexyl, cyclopentyl; and $R_6$ and $R_7$ are hydrogen or alkyl of 1 to 4 carbon atoms; and n is the integer 2-5; or c) a substituent of the formula

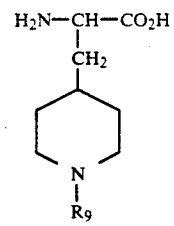

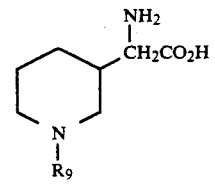

wherein $R_9$ is hydrogen, alkyl of 1 to 12 carbon atoms, phenyl or phenyl-lower-alkyl;

G is an amino acyl residue selected from the group consisting of L-leucyl, L-norleucyl and L-norvalyl;

H is D-alaninamide, D-leucinamide, glycinamide or $-NHR_5$ wherein $R_5$ is lower alkyl, cycloalkyl, fluoro lower alkyl, or $NHCONH-R_{10}$ wherein $R_{10}$ is hydrogen or lower alkyl; and the pharmaceutically acceptable salts thereof.

9. A composition according to claim 8, wherein the LHRH antagonist is N-Ac-D-Nal(2)-D-pCl-Phe-D-Trp-Ser-Tyr-D-Deh-Leu-Arg-Pro-D-AlaNH$_2$ or a pharmaceutically acceptable salt thereof.

10. A method for administering an effective amount of an LHRH agonist or antagonist, or a pharmaceutically acceptable salt thereof, which method comprises administering intranasally an aqueous solution comprising:

an effective amount of an LHRH agonist or antagonist, or a pharmaceutically acceptable salt thereof; and from about 0.2 to about 15 weight percent of a bile acid surfactant, or a pharmaceutically acceptable salt thereof in aqueous solution.

11. A method according to claim 10 which method comprises administering intranasally a nasal spray composition comprising; 0.005 to 5 mg/ml of an LHRH agonist or its pharmaceutically acceptable salt or 5 to 100 mg/ml of an LHRH antagonist or its pharmaceutically acceptable salt; and 1.5 to 5 percent by weight/volume of a bile acid surfactant or a pharmaceutically acceptable salt thereof; in a buffered aqueous solution.

* * * * *